United States Patent
Boykin et al.

(10) Patent No.: US 9,402,635 B2
(45) Date of Patent: *Aug. 2, 2016

(54) SURGICAL CUTTING INSTRUMENT WITH DUAL SURFACE INTERLOCKING COUPLING ARRANGEMENT

(71) Applicant: Medtronic PS Medical, Inc., Louisville, CO (US)

(72) Inventors: Christopher M. Boykin, Athens, TX (US); Durrell G. Tidwell, Burleson, TX (US)

(73) Assignee: Medtronic PS Medical, Inc., Fort Worth, TX (US)

( * ) Notice: Subject to any disclaimer, the term of this patent is extended or adjusted under 35 U.S.C. 154(b) by 304 days.

This patent is subject to a terminal disclaimer.

(21) Appl. No.: 14/015,189

(22) Filed: Aug. 30, 2013

(65) Prior Publication Data

US 2014/0074098 A1    Mar. 13, 2014

Related U.S. Application Data

(63) Continuation of application No. 12/136,917, filed on Jun. 11, 2008, now Pat. No. 8,523,868.

(51) Int. Cl.
*A61B 17/14* (2006.01)
*B27B 5/32* (2006.01)
(Continued)

(52) U.S. Cl.
CPC .............. *A61B 17/141* (2013.01); *A61B 17/14* (2013.01); *A61B 17/148* (2013.01); *B27B 5/32* (2013.01); *B27B 19/006* (2013.01); *A61B 2017/00477* (2013.01)

(58) Field of Classification Search
CPC ............................ A61B 17/141; A61B 17/148
See application file for complete search history.

(56) References Cited

U.S. PATENT DOCUMENTS 81,661 A * 9/1868 McDonald ...................... 83/666
173,126 A * 2/1876 Little ............................... 83/666
(Continued)

FOREIGN PATENT DOCUMENTS

DE    4036904 C1    5/1992
EP    0554929 A1    8/1993
(Continued)

OTHER PUBLICATIONS

Japanese Office Action for Japanese Publication H05-253234 for Japan Application No. 2011-513552 mailed Jul. 4, 2013.

*Primary Examiner* — Christian Sevilla
(74) *Attorney, Agent, or Firm* — Harness, Dickey

(57) ABSTRACT

A hand-held surgical cutting instrument for cutting bone material with a surgical micro-saw blade has a plurality of openings formed therein. The surgical cutting instrument includes a hand-graspable body for manipulating the cutting instrument and a blade coupling mechanism attached to the body and being configured to attach to the surgical micro-saw blade. The blade coupling mechanism includes a first coupling member including a first blade-contacting surface. The first blade-contacting surface has at least one first protrusion extending therefrom and is configured to engage a first opening in the surgical saw blade. The blade coupling mechanism includes a second coupling member including a second blade-contacting surface facing the first blade-contacting surface of the first coupling member. The second blade-contacting surface having at least one second protrusion extending therefrom and configured to engage a second opening in the surgical saw blade.

23 Claims, 5 Drawing Sheets

(51) Int. Cl.
  *B27B 19/00* (2006.01)
  *A61B 17/00* (2006.01)

(56) References Cited

U.S. PATENT DOCUMENTS

| | | | | |
|---|---|---|---|---|
| 197,650 | A | * 11/1877 | Milligan | 83/171 |
| 336,661 | A | * 2/1886 | Peck | 83/664 |
| 519,892 | A | * 5/1894 | Newton | 83/666 |
| 3,554,197 | A | 1/1971 | Dobbie | |
| 3,656,393 | A | * 4/1972 | Goellner | 83/666 |
| 3,678,934 | A | 7/1972 | Warfield et al. | |
| 3,927,893 | A | 12/1975 | Dillon et al. | |
| 3,943,934 | A | * 3/1976 | Bent | 606/178 |
| 3,952,412 | A | 4/1976 | Rhodes | |
| 3,978,862 | A | 9/1976 | Morrison | |
| 4,106,181 | A | 8/1978 | Mattchen | |
| 4,386,609 | A | 6/1983 | Mongeon | |
| 4,513,742 | A | 4/1985 | Arnegger | |
| 4,584,999 | A | 4/1986 | Arnegger | |
| 4,617,930 | A | 10/1986 | Saunders | |
| 4,620,369 | A | * 11/1986 | Gercken | 30/329 |
| 4,657,428 | A | * 4/1987 | Wiley | 403/359.3 |
| 4,739,557 | A | 4/1988 | Wagner | |
| 4,819,334 | A | 4/1989 | Mongeon | |
| 4,841,638 | A | * 6/1989 | Bardeen et al. | 30/332 |
| 5,002,555 | A | 3/1991 | Petersen | |
| 5,092,869 | A | 3/1992 | Waldron | |
| 5,122,142 | A | 6/1992 | Pascaloff | |
| 5,133,728 | A | 7/1992 | Petersen | |
| 5,135,533 | A | 8/1992 | Petersen et al. | |
| 5,178,626 | A | 1/1993 | Pappas | |
| D337,160 | S | 7/1993 | Evans | |
| 5,263,972 | A | * 11/1993 | Evans et al. | 606/176 |
| 5,265,343 | A | * 11/1993 | Pascaloff | 30/339 |
| D343,247 | S | 1/1994 | Walen | |
| D346,318 | S | 4/1994 | Evans | |
| 5,306,285 | A | * 4/1994 | Miller et al. | 606/177 |
| D348,194 | S | 6/1994 | Tanis | |
| 5,366,312 | A | * 11/1994 | Raines | 403/3 |
| D353,888 | S | 12/1994 | Raines | |
| 5,382,249 | A | * 1/1995 | Fletcher | 606/79 |
| D360,946 | S | 8/1995 | Goris | |
| D361,029 | S | 8/1995 | Goris | |
| 5,439,472 | A | 8/1995 | Evans et al. | |
| 5,440,811 | A | * 8/1995 | Challis | 30/169 |
| D362,065 | S | 9/1995 | Goris | |
| 5,468,247 | A | * 11/1995 | Matthai et al. | 606/178 |
| 5,489,285 | A | 2/1996 | Goris | |
| 5,496,316 | A | 3/1996 | Goris | |
| 5,507,763 | A | 4/1996 | Petersen et al. | |
| 5,544,511 | A | 8/1996 | Cavaleri | |
| 5,554,165 | A | * 9/1996 | Raitt et al. | 606/176 |
| 5,658,304 | A | * 8/1997 | Lim | 606/176 |
| 5,676,680 | A | 10/1997 | Lim | |
| 5,694,693 | A | * 12/1997 | Hutchins et al. | 30/166.3 |
| 5,697,158 | A | 12/1997 | Klinzing et al. | |
| 5,702,415 | A | * 12/1997 | Matthai et al. | 606/178 |
| 5,729,904 | A | * 3/1998 | Trott | 30/339 |
| 5,735,866 | A | 4/1998 | Adams et al. | |
| D394,315 | S | 5/1998 | Fisher | |
| 5,839,196 | A | 11/1998 | Trott | |
| 5,846,244 | A | 12/1998 | Cripe | |
| D404,485 | S | 1/1999 | Hutchins et al. | |
| D405,177 | S | 2/1999 | Hutchins et al. | |
| D406,223 | S | 3/1999 | Tran | |
| 5,888,200 | A | 3/1999 | Walen | |
| RE36,269 | E | 8/1999 | Wright | |
| 5,941,891 | A | 8/1999 | Walen | |
| 6,007,541 | A | 12/1999 | Scott | |
| 6,022,353 | A | 2/2000 | Fletcher et al. | |
| 6,045,564 | A | 4/2000 | Walen | |
| 6,113,618 | A | 9/2000 | Nic | |
| 6,113,619 | A | 9/2000 | Pascaloff | |
| 6,302,406 | B1 | 10/2001 | Ventura | |
| 6,332,836 | B1 | 12/2001 | Tseng | |
| D455,490 | S | 4/2002 | Pascaloff | |
| 6,367,235 | B1 | * 4/2002 | Moynihan | 56/17.5 |
| D459,805 | S | 7/2002 | Pascaloff | |
| 6,503,253 | B1 | 1/2003 | Fletcher et al. | |
| 6,656,186 | B2 | 12/2003 | Meckel | |
| 6,723,101 | B2 | 4/2004 | Fletcher et al. | |
| D489,823 | S | 5/2004 | Fisher et al. | |
| D492,412 | S | 6/2004 | Desoutter et al. | |
| 6,949,110 | B2 | 9/2005 | Ark et al. | |
| 7,001,403 | B2 | 2/2006 | Hausmann et al. | |
| 7,003,888 | B2 | 2/2006 | Bigden et al. | |
| 7,040,023 | B2 | 5/2006 | Nemazi et al. | |
| 7,147,550 | B2 | * 12/2006 | Chen | 451/520 |
| D536,791 | S | 2/2007 | Eskridge et al. | |
| 7,189,239 | B2 | 3/2007 | Fisher et al. | |
| 7,217,177 | B2 | * 5/2007 | Frech et al. | 451/359 |
| 7,258,515 | B2 | * 8/2007 | Krondorfer | 409/231 |
| 7,497,860 | B2 | * 3/2009 | Carusillo et al. | 606/82 |
| 7,833,241 | B2 | * 11/2010 | Gant | 606/176 |
| 8,523,868 | B2 | * 9/2013 | Boykin et al. | 606/82 |
| 8,852,221 | B2 | * 10/2014 | Boykin et al. | 606/171 |
| 8,920,424 | B2 | * 12/2014 | Boykin | 606/82 |
| 2002/0116023 | A1 | 8/2002 | Fletcher et al. | |
| 2002/0198556 | A1 | * 12/2002 | Ark et al. | 606/178 |
| 2003/0032971 | A1 | 2/2003 | Hausmann et al. | |
| 2004/0138668 | A1 | * 7/2004 | Fisher et al. | 606/82 |
| 2004/0258497 | A1 | * 12/2004 | Krondorfer | 409/232 |
| 2005/0192585 | A1 | * 9/2005 | Simmons | 606/82 |
| 2007/0088330 | A1 | 4/2007 | House | |
| 2008/0027449 | A1 | * 1/2008 | Gundlapalli et al. | 606/82 |
| 2008/0119860 | A1 | 5/2008 | McCarthy | |
| 2008/0190259 | A1 | * 8/2008 | Bohne | 83/666 |
| 2008/0243125 | A1 | * 10/2008 | Guzman et al. | 606/82 |
| 2009/0138017 | A1 | * 5/2009 | Carusillo et al. | 606/82 |
| 2009/0312779 | A1 | * 12/2009 | Boykin et al. | 606/171 |
| 2010/0052269 | A1 | * 3/2010 | Zaiser et al. | 279/144 |
| 2010/0056029 | A1 | * 3/2010 | Grunikiewicz | 451/442 |
| 2010/0292701 | A1 | * 11/2010 | Fisher et al. | 606/82 |
| 2013/0204256 | A1 | * 8/2013 | Wang et al. | 606/82 |
| 2015/0025535 | A1 | 1/2015 | Boykin et al. | |
| 2015/0112347 | A1 | * 4/2015 | Boykin | 606/82 |
| 2015/0128402 | A1 | * 5/2015 | Wang et al. | 29/453 |

FOREIGN PATENT DOCUMENTS

| | | |
|---|---|---|
| EP | 0776634 A2 | 6/1997 |
| JP | H05253234 A | 10/1993 |
| WO | WO-9513020 A1 | 5/1995 |
| WO | WO-2007041027 A2 | 4/2007 |

* cited by examiner

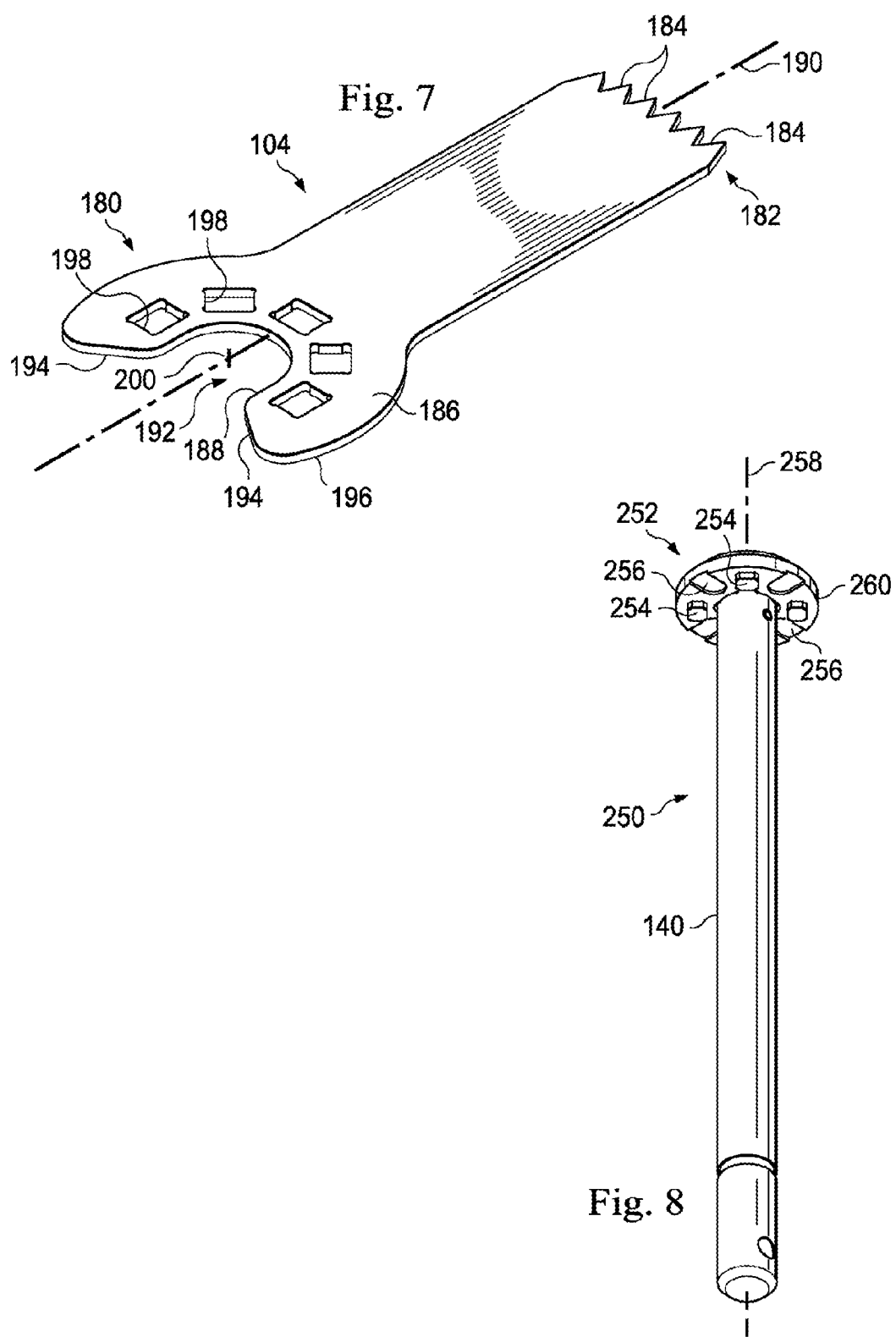

SURGICAL CUTTING INSTRUMENT WITH DUAL SURFACE INTERLOCKING COUPLING ARRANGEMENT

CROSS-REFERENCE TO RELATED APPLICATIONS

This application is a continuation of U.S. patent application Ser. No. 12/136,917 filed on Jun. 11, 2008. The entire disclosure of the above application is incorporated herein by reference.

The present disclosure is related to commonly owned U.S. application Ser. No. 12/136,935 filed on Jun. 11, 2008, titled, "Surgical Cutting Instrument with Near-Perimeter Interlocking Coupling Arrangement", incorporated herein in its entirety by reference.

FIELD OF THE INVENTION

The present disclosure relates to a surgical cutting instrument, and more particularly, to a surgical cutting instrument with a dual surface interlocking coupling arrangement.

BACKGROUND

Bone-cutting surgical saws, such as sagittal or oscillating type surgical saws, cut most effectively at very high speeds, such as for example, 10000-40000 cycles per minute. These high speeds introduce high levels of vibration and can cause blade wander during a cut. Accordingly, actual blade cuts frequently have a thickness considerably greater than the thickness of the actual blade. For example, a cutting blade having a 0.015 inch thickness may be unable to cut a groove having a width of less than 0.030 inch.

Some vibration may be due to ineffective coupling systems. Coupling systems on conventional micro-saws clamp each side of the blade to rigidly secure the blade in place. Typical systems include protrusions on a bottom clamp that penetrate openings in the blade, and include an opposing top clamp that is smooth. Accordingly, only the bottom clamp holds the blade, while the top clamp is simply a smooth guide for blade placement. Over time, clamping forces may decrease, and because only one clamp secures the blade, the system becomes less stable, introducing additional vibration in the blade, and possibly resulting in less cutting effectiveness.

The devices disclosed herein overcome one or more of short-comings in the prior art.

SUMMARY

In one aspect, the present disclosure is directed to a hand-held surgical cutting instrument for cutting bone material with a surgical micro-saw blade having a plurality of openings formed therein. The surgical cutting instrument includes a hand-graspable body for manipulating the cutting instrument and a blade coupling mechanism attached to the body and is configured to attach to the surgical micro-saw blade. The blade coupling mechanism includes a first coupling member including a first blade-contacting surface. The first blade-contacting surface has at least one first protrusion extending therefrom and is configured to engage a first opening in the surgical saw blade. The blade coupling mechanism includes a second coupling member including a second blade-contacting surface facing the first blade-contacting surface of the first coupling member. The second blade-contacting surface has at least one second protrusion extending therefrom and is configured to engage a second opening in the surgical saw blade.

In another exemplary aspect, the present disclosure is directed to a hand-held surgical cutting system for cutting bone material. The system includes a surgical micro-saw blade having a distal end and a proximal end. The distal end has cutting teeth formed thereon and the proximal end has through-openings formed therein. The system also includes a surgical cutting saw including a hand-graspable body and a blade coupling mechanism attached to the body and configured to attach to the surgical micro-saw blade. The blade coupling mechanism includes a first coupling member including a first blade-contacting surface. The first blade-contacting surface has a first plurality of protrusions extending therefrom and is configured to engage openings in the surgical saw blade. The first plurality of protrusions are symmetrically disposed on the first blade-contacting surface. The blade coupling mechanism also includes a second coupling member including a second blade-contacting surface facing the first blade-contacting surface of the first coupling member. The second blade-contacting surface has a second plurality of protrusions extending therefrom and is configured to engage openings in the surgical saw blade. The second plurality of protrusions may be symmetrically disposed on the second blade-contacting surface and are offset from the first plurality of protrusions.

In yet another exemplary aspect, the present disclosure relates to a hand-held surgical cutting instrument for cutting bone tissue with a surgical micro-saw blade having openings formed therein. The surgical cutting instrument includes a hand-graspable body for manipulating the cutting instrument and a collet assembly attached to the body for attaching to the surgical micro-saw blade. The collet assembly includes a driving shaft including a head portion and a shaft portion. The head portion is removably connected to a first end of the shaft portion and includes a first blade-contacting surface facing the shaft portion. The blade-contacting surface has a first plurality of protrusions extending therefrom and is configured to engage the openings in the surgical saw blade. The collet assembly also includes a sleeve disposed about the driving shaft and is axially movable relative to the driving shaft. The sleeve includes a second blade-contacting surface facing the first blade-contacting surface. The second blade-contacting surface has a second plurality of protrusions extending therefrom and is configured to engage openings in the surgical saw blade. The first plurality of protrusions are offset from the second plurality of protrusions. At least one of the first and second blade-contacting surfaces includes a plurality of receiving recesses formed therein, the receiving recesses are sized and shaped to receive the respective protrusions of the other of the at least one of the first and second blade-contacting surfaces.

These and other features will become apparent from the following description.

BRIEF DESCRIPTION OF THE DRAWINGS

FIG. 7 is an illustration of an exemplary micro-saw blade from the bone-cutting surgical system of FIG. 1.

FIG. 8 is an illustration of an alternative embodiment of a driving shaft usable in an a collet assembly.

DETAILED DESCRIPTION

Figure 1:
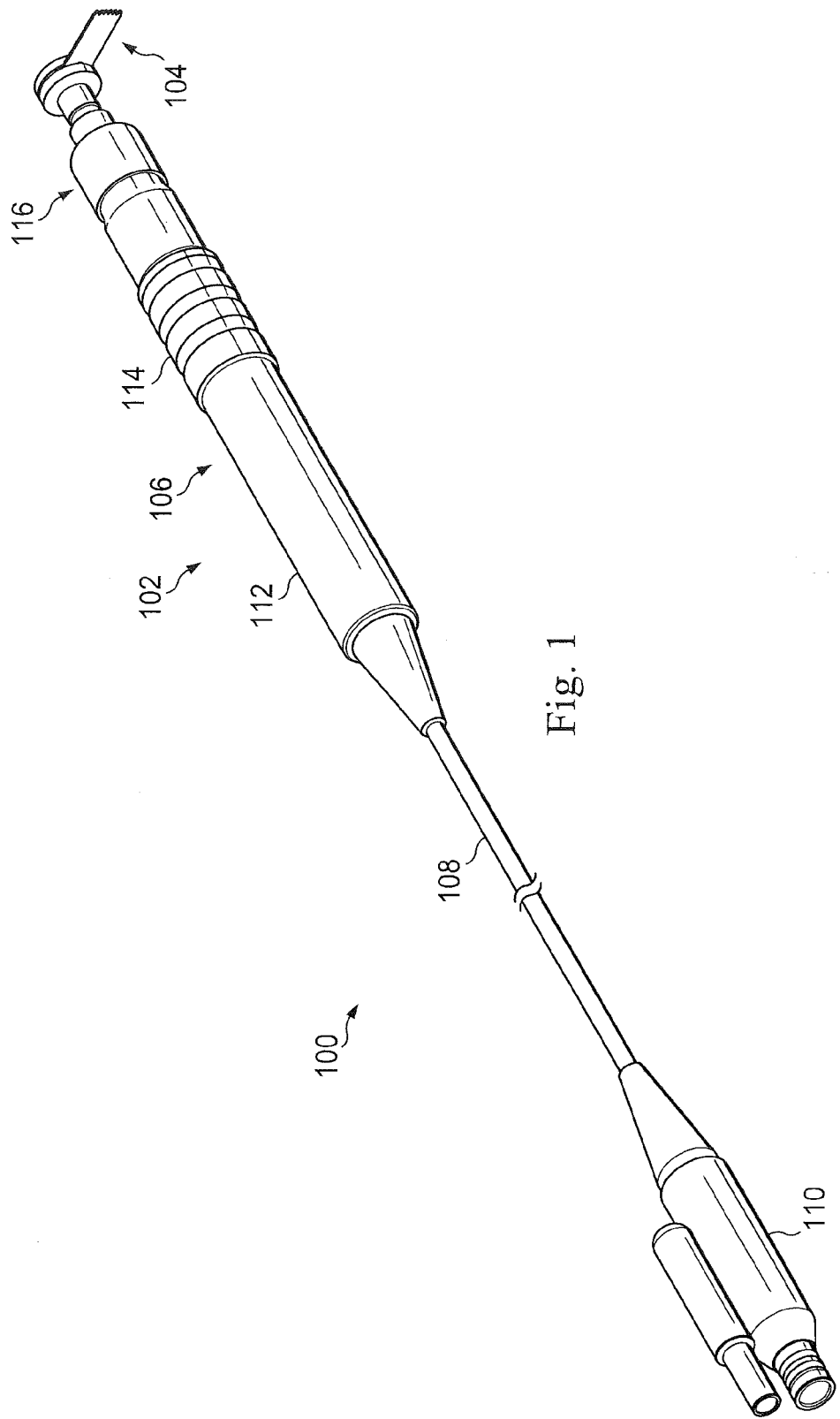
FIG. 1 is an illustration of an exemplary oscillating bone-cutting surgical system.

For the purposes of promoting an understanding of the principles of the invention, reference will now be made to embodiments or examples illustrated in the drawings, and specific language will be used to describe the same. It will nevertheless be understood that no limitation of the scope of the invention is thereby intended. Any alteration and further modifications in the described embodiments, and any further applications of the principles of the invention as described herein are contemplated as would normally occur to one skilled in the art to which the disclosure relates.

Generally, the present disclosure relates to a bone cutting surgical system including a hand-held, high-speed, bone-cutting surgical saw, such as a sagittal or oscillating saw, and a cutting micro-saw blade. The saw includes a collet assembly with protrusions, such as pins or nubs, that mesh with or extend into openings on the cutting blade, thereby securing the blade in place in the collet assembly. In order to improve blade stability, the collet assembly disclosed herein includes protrusions that project into opening in the micro-saw blade from both the upper and lower sides. These offsetting protrusions may equalize the blade attachment, may reduce vibration, and may improve overall blade stability. In turn, this may improve cutting accuracy, which can reduce patient trauma and speed recovery time.

Turning now to FIG. 1, the present disclosure is directed to a bone-cutting surgical system 100 including a surgical saw 102 and a selectively removable micro-saw blade 104. The surgical saw 102 includes a hand-piece 106, a cord 108, and a connector 110 configured to removably couple with a power source. The connector 110 is merely exemplary, and it should be apparent to one skilled in the art that any suitable connector may be used, and in some embodiments, the cord 108 itself may be coupled to the power source without the use of a connector. Additional contemplated embodiments include a power source as a part of the hand-piece 106, such as a battery powered hand-piece.

The hand-piece 106 includes a motor assembly 112, a grip 114, and a collet assembly 116. In some embodiments, the motor assembly 112 is housed within the grip 114, while in other embodiments, it is disposed adjacent to the grip 114. It is contemplated that any suitable system for controlling the surgical saw 102 may be used. For example, some embodiments include a trigger system disposed on the hand-piece 106 to provide hand-control of the cutting speed, or alternatively, a foot pedal associated with the hand-piece 106 through the power source to provide the controlling inputs. Other control systems also are contemplated.

Figure 2:
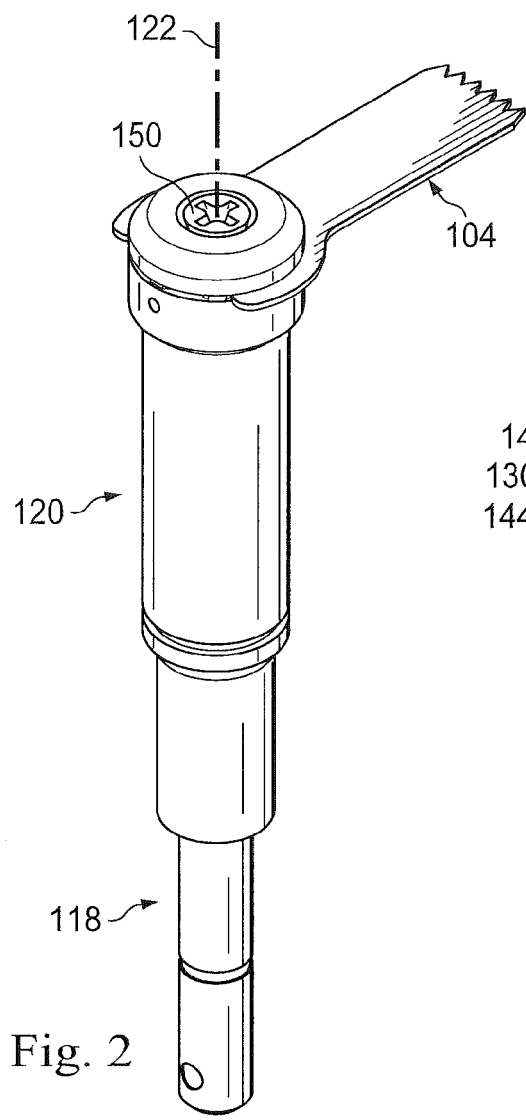
FIG. 2 is an illustration of a portion of an exemplary collet assembly from the surgical system of FIG. 1 with a micro-saw blade.
Figure 3:
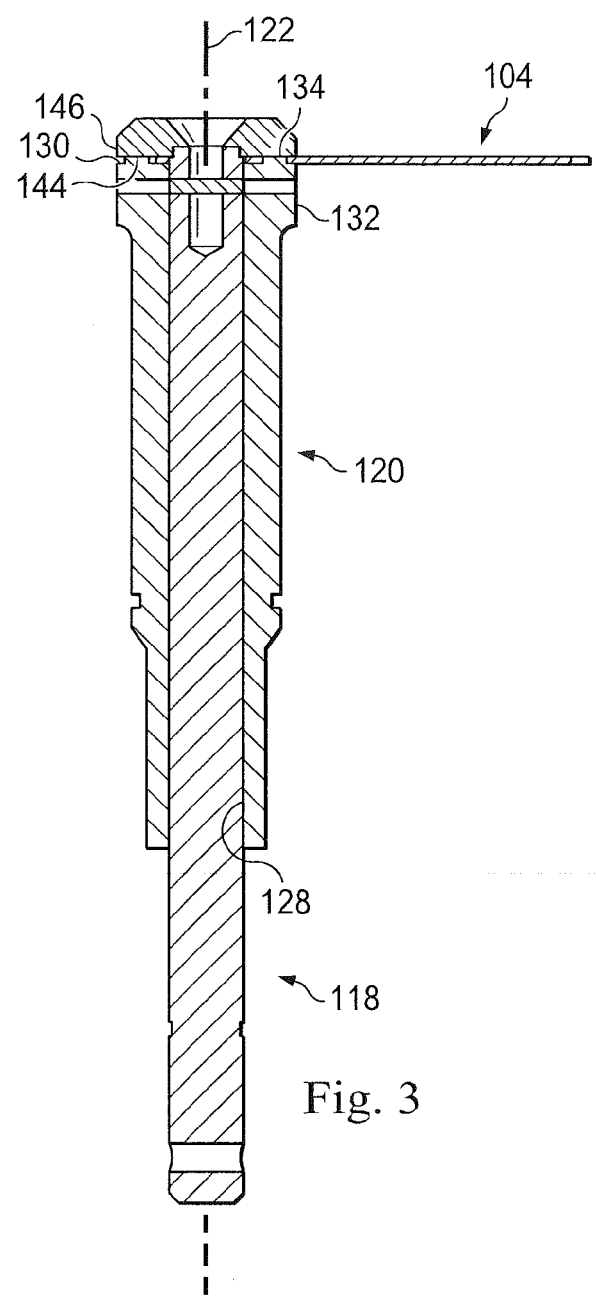
FIG. 3 is an illustration of a cross-section of the exemplary collet assembly of FIG. 2 with the micro-saw blade.
Figure 4:
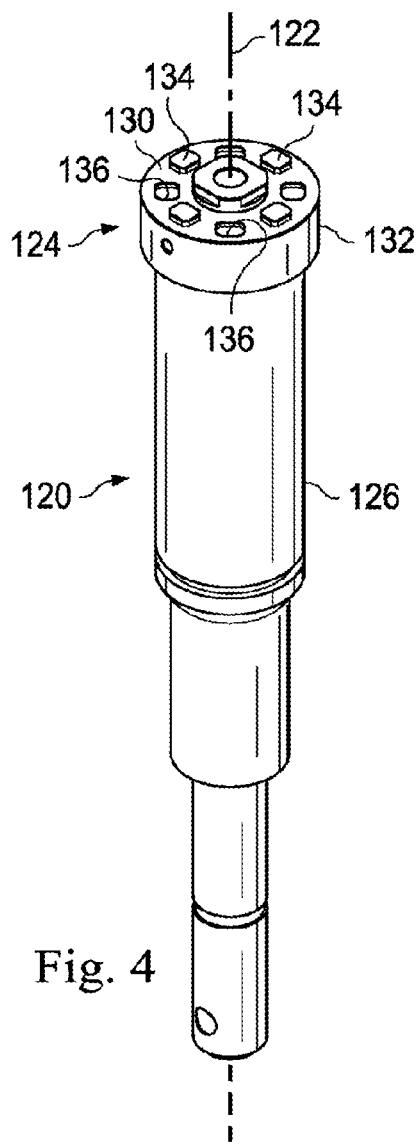
FIG. 4 is an illustration of the collet assembly of FIG. 2 with a driving shaft head removed to show a blade-contacting surface on a sleeve.
Figure 5:
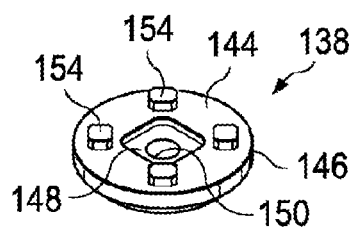
FIG. 5 is an illustration of an exemplary driving shaft head of the collet assembly of FIG. 2, showing a blade-contacting surface.
Figure 6:
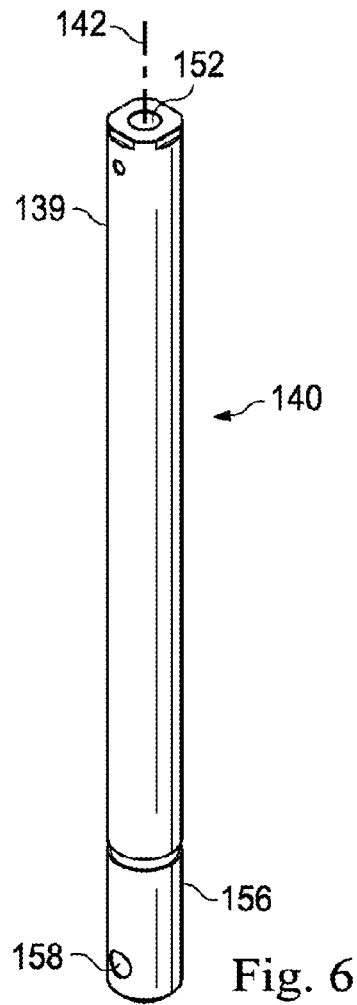
FIG. 6 is an illustration of an exemplary driving shaft shank of the collet assembly of FIG. 2.

FIGS. 2 and 3 show a portion of the exemplary collet assembly 116, and FIGS. 4-6 show collet assembly components. Referring to FIGS. 2 and 3, the collet assembly 116 secures the saw blade 104 to the surgical saw 102 and transfers a driving force from the motor to the blade. In this embodiment, it includes a driving shaft 118 and a sleeve 120 defining a longitudinal collet axis 122. The sleeve 120 receives and extends about the driving shaft 118 and is axially movable along the collet axis 122 relative to the driving shaft 118, enabling selective coupling with the blade 104. It is contemplated that any suitable material may be used for the collet assembly 116. In one embodiment, a biocompatible stainless steel material, such as Stainless 17-4 is used.

Referring to FIGS. 3 and 4, the sleeve 120 includes a head 124 and a shank 126, with a central bore 128 extending therethrough. In FIG. 4, a portion of the driving shaft 118 is disposed within the bore 128. The bore 128 permits the sleeve 120 to move axially along the driving shaft 118, enabling selective locking and releasing of the blade 104. The head 124 includes a substantially planar blade-contacting surface 130 and an outer perimeter 132 adjacent the blade-contacting surface 130.

The blade-contacting surface 130 includes a plurality of protrusions 134 formed thereon. These are symmetrically disposed about the collet axis 122 and are configured to interface with the saw blade 104. Here, the sleeve 120 includes four protrusions 134 extending therefrom, spaced apart about the collet axis 122 at 90 degree intervals. It is contemplated that more or fewer protrusions 134 may be present. The protrusions 134 may be integrally formed with sleeve 120 or, for manufacturing convenience, may be separate components fit, such as with an interference fit, into receiving ports (not shown) formed in the blade-contacting surface 130. In this embodiment, the protrusions 134 are rectangular projections having a height equal to or greater than the thickness of a corresponding saw blade 104. In other examples however, the protrusions 134 have a circular, triangular, or diamond-shaped cross-section. Protrusions of other shapes are also contemplated.

In addition to the protrusions, the blade-contacting surface 130 includes a plurality of receiving recesses 136. In FIG. 4, each of these is disposed between adjacent protrusions 134, spaced symmetrically about the collet axis 122. Like the protrusions 134, the receiving recesses 136 are spaced 90 degrees apart. These have a depth less than the height of the adjacent protrusions, and as discussed below, are sized to receive protrusions on the driving shaft 118.

The driving shaft 118 is shown in greater detail in FIGS. 3, 5, and 6. Here, the driving shaft 118 includes a head 138 removably coupled to a distal end 139 of a shaft 140. The shaft 140 defines a longitudinally extending shaft axis 142 (FIG. 6).

Referring to FIGS. 3 and 5 the head 138 includes a blade-contacting surface 144 and an outer perimeter 146. Here, the blade-contacting surface 144 includes a central recess 148 for connecting with the distal end 139 of the shaft 140. In this embodiment, the central recess 148 is square shaped. The distal end 139 of the shaft 140 also is grooved to be square-shaped so that when the driving shaft 118 is assembled, the head 138 is unable to rotate relative to the shaft 140. A through hole 150 in the central recess 148 receives a fastener, such as a screw 150 (shown in FIG. 2) that extends into a corresponding bore 152 in the end of the distal end 139 of the shaft 140 to fasten the head 138 to the shaft 140.

The blade-contacting surface 144 also includes protrusions 154 formed thereon. Like those on the sleeve, these are symmetrically disposed about the collet axis 122 and are configured to interface with the saw blade 104. Here, the head 138 includes four protrusions 154 extending therefrom, spaced apart at 90 degree intervals. It is contemplated that more or fewer protrusions 154 may be present. The protrusions 154 may be integrally formed with head 138 or may be separate components fit into receiving ports. Like those on the sleeve 120, the protrusions 154 are rectangular projections having a height equal to or greater than the thickness of the corresponding saw blade 104. Protrusions of other shapes are also contemplated. As discussed below, these protrusions are shaped and sized to fit into the receiving recess formed in the sleeve 120.

The shaft 140 includes the distal end 139 either connected to or integral with the head 138 and includes a proximal end 156. In this embodiment, the proximal end 156 includes a motor coupling feature 158 shown as a pin-receiving through passage that connects either directly or cooperatively to the motor to provide the cutting oscillation required.

Referring now to FIG. 3, as can be seen, the sleeve blade-contacting surface 130 and the driving shaft blade-contacting surface 144 face each other. The outer perimeter 146 of the head 138 is sized to have substantially the same diameter as the sleeve outer perimeter 132. The sleeve 120 and driving shaft 118 may axially move apart to receive the blade 104, and then come together to clamp the blade 104 between the blade-contacting surfaces 130, 144. Although not shown, a spring force may be used to bias the sleeve 120 into a clamped position to secure any blade in place.

FIG. 7 shows the exemplary micro-saw blade 104 usable with the surgical saw 102 in FIG. 1 and securable with the collet assembly 116 in FIGS. 2-6. The micro-saw blade 104 may be stamped and/or machined form a single material having a thickness in the range of 0.007-0.022 inch, for example. It includes a proximal end 180 that facilitates interconnection with the collet assembly 116 and a distal end 182 having a cutting edge including a plurality of cutting teeth 184 formed thereon.

In this example, the proximal end 180 is defined by a relatively bulbous head 186 that includes a slot 188 extending inwardly along a longitudinal axis 190 from the proximal end of the saw blade 104. The slot 188 is formed with a funnel-like opening 192 defined by substantially straight edges 194 facing toward the longitudinal axis 190. The straight edges 194 may help guide the saw blade 104 into place on the collet assembly 116. A partially circular outer perimeter 196 defines an outer edge of the bulbous head 186. In some embodiments, the outer perimeter 196 has a diameter substantially the same as, or slightly smaller than, the diameter of the driving shaft head 138 and the sleeve head 124.

Openings 198 formed in the proximal end 180 permit the saw blade 104 to be secured to the surgical saw collet assembly 116. In the embodiment shown, the openings 198 are symmetrically disposed about a center point 200. Here, at least two openings 198 lie directly on opposing sides of the center point 200 and on transverse sides of the longitudinal axis 190. A centrally disposed opening 198 lies along the longitudinal axis 190. In the example shown the openings 198 are offset from each other by 45 degrees and are sized to match the protrusions 134, 154 on the driving shaft 118 and sleeve 120. However, other offset angles are contemplated that match the desired collet assembly.

Here, each opening 198 is rectangular shaped in order to match the shape of the protrusions of the collet assembly 116. In the example shown, the bulbous head 186 includes five openings 204, 206. However, in other embodiments, more or less openings may be provided. When the funnel-like opening 192 has an angle smaller than that shown, additional openings may be included, while maintaining the 45 degree spacing shown.

Returning to FIG. 3, the collet protrusions interconnect with the saw blade 104 to secure it in place. The sleeve protrusions 134 extend upwardly in FIG. 3, through the openings 198 and abut against the blade-contacting surface 144. Likewise, although not visible in FIG. 3, the driving shaft protrusions 154 extend downwardly through the openings 198 and into the receiving recesses 136 in the sleeve 120. Accordingly, in the saw blade embodiment having five openings 198 as in FIG. 7, either two or three protrusions pass through the blade openings 198 from the bottom and either two or three protrusions pass through the blade openings 198 from the top. Because the sleeve protrusions 134 are spaced 90 degrees apart and the driving shaft protrusions 154 are spaced 90 degrees apart, but offset from the sleeve protrusions by 45 degrees, the blade 104 can be removed and secured in the collet assembly in eight different positions. In some embodiments, for example, the collet assembly includes a total of only four protrusions or six protrusions, and the openings on the blade 104 are chosen to correspond with the protrusions. Other amounts of protrusions are contemplated.

In addition to securing the saw blade 104 in place with the protrusions 134, 154, the blade-contacting surfaces 130, 134 also frictionally engage and reduce vibration and play. Accordingly, it may be beneficial to provide as much contact area between the blade and blade-contacting surfaces as is practicable. Accordingly, in the embodiment shown, the protrusions 134, 154 are formed with rectangular cross-sections instead of circular cross-sections. Rectangular shaped protrusions can have the same maximum width as a corresponding cylindrical protrusions for stability, but permits an overall increase in the blade surface area that interfaces with the blade-contacting surfaces 130, 144. This too may help more solidly secure the blade 104 in place in the collet assembly 116.

FIG. 8 shows an alternative driving shaft 250. Here the driving shaft includes the shaft 140, but includes an alternative head 252. Because many of the features of the head 252 are similar to those discussed above, only the differences will be discussed in detail. Here, in addition to having rectangular protrusions 254, the head 252 includes a plurality of receiving recesses 256. Each of these are disposed between the adjacent protrusions 254, and spaced symmetrically about a driving shaft axis 258. The protrusions 254 are spaced 90 degrees apart, and the receiving recesses are spaced 90 degrees apart. These receiving recesses 256 are shaped differently than the corresponding protrusions on the sleeve 120 however. These receiving recesses 256 are shaped with a curved inner end and parallel sides that extend entirely to an outer perimeter 260. Accordingly, in use with this embodiment, the sleeve protrusions 134 may extend entirely through the blade openings 198, but instead of abutting directly against the blade-contacting surface of the driving shaft, the sleeve protrusions project into the receiving recesses 256.

It should be noted that in some embodiments, the receiving recesses on the head may be shaped and sized similar to those described relative to the sleeve 120, but that any suitable size and shape may be used.

Figure 9:
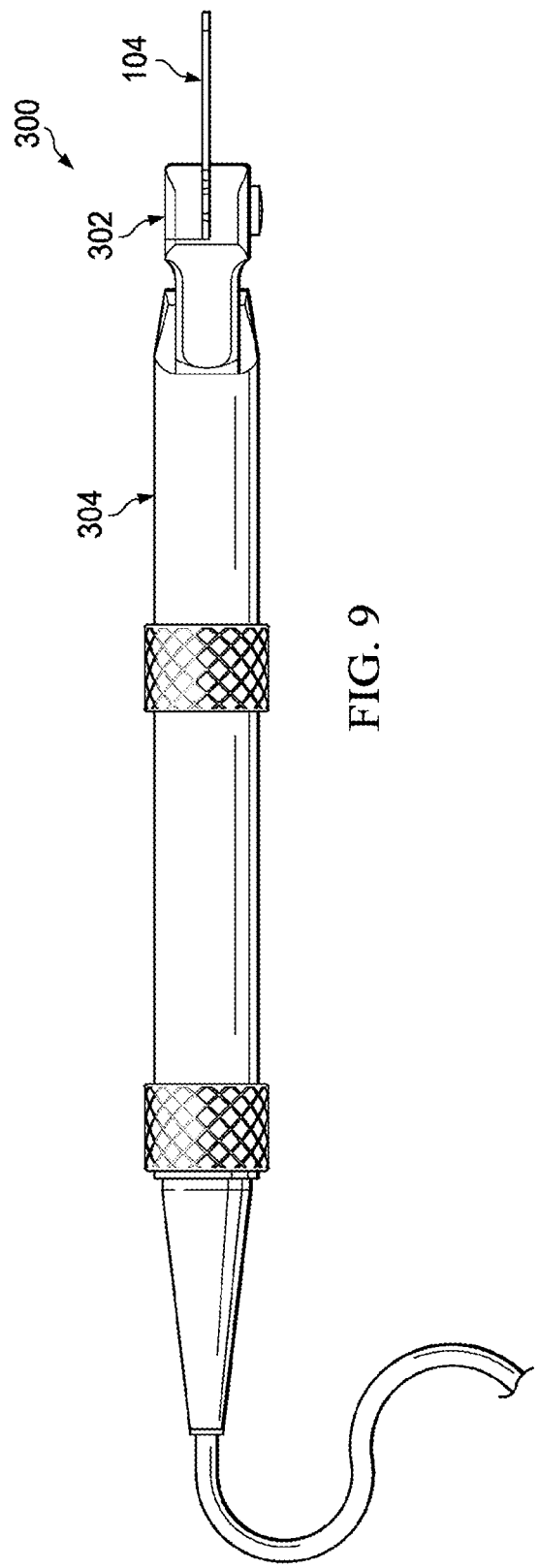
FIG. 9 is an illustration of an exemplary sagittal bone-cutting surgical system.

FIG. 9 shows a sagittal saw 300 for driving the saw blade 104. In this embodiment, a collet assembly 302 is arranged to secure the blade 104 in an axial direction relative to a saw handle 304. Accordingly, in this embodiment, the collet assembly 302 includes side-by-side blade-contacting surfaces. However, like the oscillating saw 102 disclosed in FIGS. 1-6, the sagittal saw 300 includes protrusions disposed on both blade-contacting surfaces adjacent an exterior edge of the collet fixture, and the blade 104 is sized so that the outer perimeter of the head of the saw blade substantially corresponds to the edge of the collet assembly.

Although only a few exemplary embodiments have been described in detail above, those skilled in the art will readily appreciate that many modifications are possible in the exemplary embodiments without materially departing from the novel teachings and advantages of this disclosure. Accordingly, all such modifications and alternatives are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure.

We claim:

1. A surgical cutting instrument for cutting bone material with a blade, comprising:
    a hand-graspable body for manipulating the cutting instrument;
    a blade coupling mechanism attached to the hand-graspable body and being configured to attach to the blade, the blade coupling mechanism comprising:
        a first coupling member including a first blade-contacting surface, the first blade-contacting surface having at least one first protrusion extending therefrom and configured to engage the blade; and
        a second coupling member including a second blade-contacting surface facing the first blade-contacting surface of the first coupling member, the second blade-contacting surface having at least one second protrusion extending therefrom and configured to engage the blade.

2. The surgical cutting instrument of claim 1, further comprising:
    a blade receiving region defined between the first blade-contacting surface and the second blade-contacting surface;
    wherein the at least one first protrusion and the at least one second protrusion extend into the blade receiving region.

3. The surgical cutting instrument of claim 2, wherein the blade receiving region is variable in a dimension based on a position of at least one of the first coupling member or the second coupling member.

4. The surgical cutting instrument of claim 2, wherein at least one of the first blade-contacting surface or the second blade-contacting surface has a recess formed therein to receive the at least one first protrusion or the at least one second protrusion.

5. The surgical cutting instrument of claim 4, wherein the at least one first protrusion includes a first four protrusions symmetrically spaced 90 degrees apart, and the at least one second protrusion includes a second four protrusions symmetrically spaced 90 degrees apart, the each second protrusion of the second four protrusions being offset from each first protrusion of the first four protrusions by 45 degrees.

6. The surgical cutting instrument of claim 5, wherein the recess includes a first four recesses spaced 90 degrees apart in the first blade-contacting surface and a second four recesses spaced 90 degrees apart in the second blade-contacting surface, the second four recesses being offset from the first four recesses by 45 degrees.

7. The surgical cutting instrument of claim 5, further comprising:
    a shaft portion that extends normal to the first blade-contacting surface and through the second blade-contacting surface.

8. The surgical cutting instrument of claim 1, wherein the first coupling member comprises a head and a shaft, wherein the head is removably connected to the shaft and the first blade-contacting surface is formed on the head.

9. The surgical cutting instrument of claim 8, wherein the first blade-contacting surface includes a central bore and the shaft extends through the central bore.

10. The surgical cutting instrument of claim 9, wherein the shaft extends along a shaft axis;
    wherein the blade coupling mechanism is configured to engage the blade such that the blade extends transverse to the shaft axis.

11. The surgical cutting instrument of claim 1,
    wherein the blade is secured axially relative to the hand-graspable body and the first blade-contacting surface is side-by-side the second blade-contacting surface.

12. The surgical cutting instrument of claim 1, wherein the at least one first protrusion is adjacent a first exterior edge of the first coupling member; and
    wherein the at least one second protrusion is adjacent a second exterior edge of the second coupling member.

13. A surgical cutting instrument for cutting bone material with a blade, comprising:
    a hand-graspable body for manipulating the cutting instrument;
    a blade coupling mechanism attached to the hand-graspable body defining a blade receiving region to receive the blade, the blade coupling mechanism comprising:
        a first coupling member including a first blade-contacting surface, at least one first protrusion extending therefrom, and at least one first recess formed in the first blade-contacting surface; and
        a second coupling member including a second blade-contacting surface, at least one second protrusion extending therefrom, and at least one second recess formed in the second blade-contacting surface;
        wherein the at least one first protrusion is positioned near an external perimeter of the first coupling member;
    a shaft portion extending from the first coupling member and through a bore formed in the second coupling member.

14. The surgical cutting instrument of claim 13, wherein the at least one first recess is formed into the first blade-contacting surface and extends to the external perimeter of the first coupling member.

15. The surgical cutting instrument of claim 13, wherein the bore is substantially a central bore through the second coupling member.

16. The surgical cutting instrument of claim 13, further comprising:
    a sleeve moveable relative to the shaft portion;
    wherein the second coupling member is defined by the sleeve.

17. The surgical cutting instrument of claim 13, wherein the first coupling member and the shaft portion are separate members fixable together.

18. The surgical cutting instrument of claim 13, wherein the first coupling member and the shaft portion are integrally formed.

19. The surgical cutting instrument of claim 13, further comprising:
    a motor at least partially positioned within the hand-graspable body.

20. The surgical cutting instrument of claim 19, wherein the shaft portion includes a motor coupling feature to couple to the motor to provide a cutting oscillation to the blade.

21. A surgical cutting instrument for cutting bone material with a blade, comprising:
- a hand-graspable body for manipulating the cutting instrument;
- a motor associated with the hand-graspable body;
- a blade coupling mechanism associated with the hand-graspable body, comprising:
  - a first coupling member having a first blade-contacting surface, and
  - a second coupling member having a second blade-contacting surface;
- a shaft portion extending from the first coupling member and through a bore formed in the second coupling member; and
- a sleeve having a bore extending through the sleeve and through which the shaft portion extends, wherein the sleeve is moveable relative to the shaft portion;
- wherein the shaft portion is coupled to the motor to provide a cutting oscillation to the blade.

22. The surgical cutting instrument of claim 21, wherein the second coupling member is formed at a distal end of the sleeve.

23. The surgical cutting instrument of claim 22, wherein the sleeve is configured to move relative to the shaft portion to move the first coupling member relative to the second coupling member to enable selective locking and releasing of the blade.

* * * * *